(12) United States Patent
Hasegawa

(10) Patent No.: US 10,477,947 B2
(45) Date of Patent: Nov. 19, 2019

(54) COSMETIC CONTAINER

(71) Applicant: AMG CO., Ltd., Tokyo (JP)

(72) Inventor: Hiroki Hasegawa, Tokyo (JP)

(73) Assignee: AMG Co., Ltd., Tokyo (JP)

( * ) Notice: Subject to any disclaimer, the term of this patent is extended or adjusted under 35 U.S.C. 154(b) by 0 days.

(21) Appl. No.: 16/094,749

(22) PCT Filed: May 31, 2018

(86) PCT No.: PCT/JP2018/021057
§ 371 (c)(1),
(2) Date: Oct. 18, 2018

(87) PCT Pub. No.: WO2018/230353
PCT Pub. Date: Dec. 20, 2018

(65) Prior Publication Data
US 2019/0200731 A1 Jul. 4, 2019

(30) Foreign Application Priority Data
Jun. 13, 2017 (JP) ................................. 2017-116118

(51) Int. Cl.
*A45D 44/00* (2006.01)
*A61K 8/02* (2006.01)
*F17C 13/00* (2006.01)

(52) U.S. Cl.
CPC .......... *A45D 44/002* (2013.01); *A61K 8/0212* (2013.01); *F17C 13/002* (2013.01); *A45D 2200/25* (2013.01); *F17C 2221/012* (2013.01)

(58) Field of Classification Search
CPC .............. A45D 44/002; A45D 2200/25; A61K 8/0212; F17C 13/002; F17C 2221/012
See application file for complete search history.

(56) References Cited

FOREIGN PATENT DOCUMENTS

| JP | 11-046858 A | 2/1999 |
|---|---|---|
| JP | 2014-015224 A | 1/2014 |
| JP | 2014-508691 A | 4/2014 |
| JP | 2016-043110 A | 4/2016 |
| JP | 2017-099941 A | 6/2017 |
| JP | 3210878 U | 6/2017 |

OTHER PUBLICATIONS

Japan Patent Office, International Search Report for PCT Application No. PCT/JP2018/021057, dated Jul. 31, 2018.
Japan Patent Office, Written Opinion of the International Searching Authority for PCT Application No. PCT/JP2018/021057, dated Jul. 31, 2018.

*Primary Examiner* — Michael C Miggins
(74) *Attorney, Agent, or Firm* — SoCal IP Law Group LLP; Angelo Gaz

(57) ABSTRACT

There is disclosed herein a cosmetic container capable of dissolving hydrogen in a cosmetic composition and maintaining a state in which hydrogen is dissolved for a long period of time. A cosmetic container for storing a cosmetic composition includes a container main body formed of a hydrogen impermeable material, and a plurality of hydrogen storage portions and filled with hydrogen gas, at least one of which is formed of a hydrogen permeable sheet, wherein the hydrogen permeability of the hydrogen permeable sheet through which hydrogen gas permeates is configured to be different among the plurality of the hydrogen storage portions, and the hydrogen permeable sheets of the plurality of the hydrogen storage portions are configured so as to come into close contact with the cosmetic composition stored in the container main body.

9 Claims, 10 Drawing Sheets

Fig.3
(a)
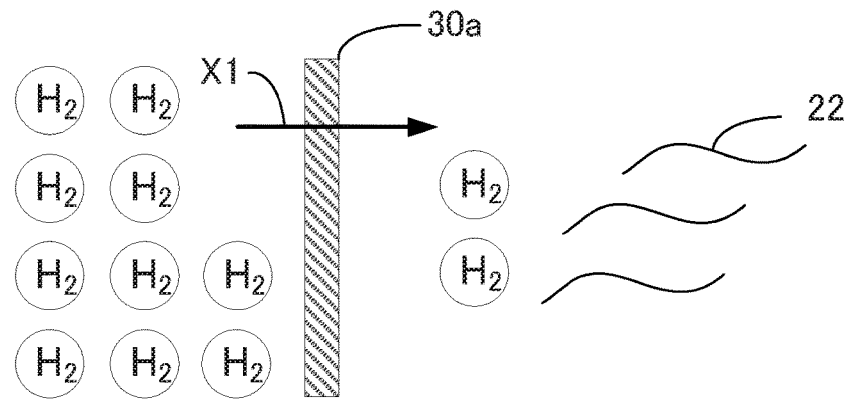
(b)
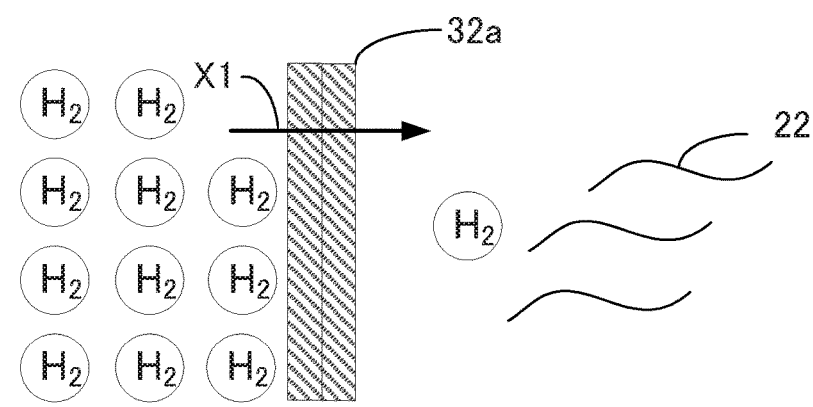
(c)
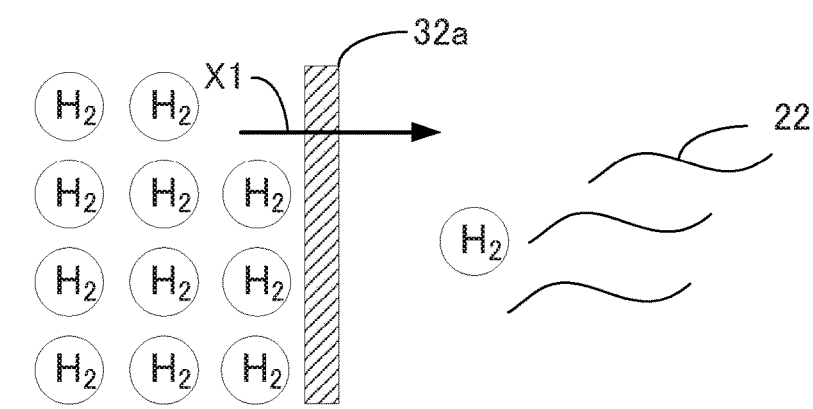

COSMETIC CONTAINER

RELATED APPLICATION INFORMATION

This application claims priority to International PCT Application No. PCT/JP2018/021057, filed May 31, 2018 entitled "Cosmetic Container," which claims priority to Japanese Patent Application No.: 2017-116118 filed Jun. 13, 2017, all of which are incorporated herein by reference in their entirety.

TECHNICAL FIELD

The present invention relates to a cosmetic container.

BACKGROUND ART

Conventionally a face mask for a face formed with a base material sheet impregnated with a cosmetic composition such as a cosmetic lotion has been used for cosmetic purposes (for example, Patent Literature 1).

It is known that the cosmetic composition improves the cosmetic effect by including hydrogen.

CITATION LIST

Patent Literature

[Patent Literature 1] JP H9-313248A

SUMMARY OF INVENTION

Technical Problem

Even when the cosmetic composition is sealed in a hydrogen impermeable material like an aluminum package, there is a problem that hydrogen gradually escapes.

In view of the above, the present invention provides a cosmetic container capable of dissolving hydrogen into a cosmetic composition and maintaining a state in which hydrogen is dissolved for a long period of time.

Solution to Problem

A first invention is a cosmetic container for storing a cosmetic composition, including a container main body formed of a hydrogen impermeable material, and a plurality of hydrogen storage portions filled with hydrogen gas, at least one of which is formed of a hydrogen permeable sheet, wherein the hydrogen permeability of the hydrogen permeable sheet through which hydrogen gas permeates is configured to be different among the plurality of the hydrogen storage portions, and the hydrogen permeable sheets of the plurality of the hydrogen storage portions are configured so as to come into close contact with the cosmetic composition stored in the container main body.

In order to keep hydrogen dissolved in the cosmetic composition over a long period of time, it is sufficient to allow hydrogen gas to permeate from the hydrogen storage portion in small amounts, but if too small, there may be cases where the amount of hydrogen contained in the cosmetic composition is insufficient at the time of cosmetic composition usage by the user. In this regard, the inventor of the present invention arrived at a structure for relatively quickly including a substantial amount of hydrogen in the cosmetic composition and a structure for maintaining the amount of hydrogen contained. According to the configuration of the first invention, since the hydrogen permeability is different among the plurality of hydrogen storage portions, even after the hydrogen gas is exhausted from one of the hydrogen storage portions, hydrogen gas discharge from another of the hydrogen storage portions continues and hydrogen gas penetration into the cosmetic composition continues. That is, even if a substantial amount of hydrogen gas dissolves relatively quickly into the cosmetic composition and then hydrogen gas escapes from the cosmetic composition, new hydrogen gas continues to dissolve into the cosmetic composition. This makes it possible to maintain a state in which hydrogen is dissolved in the cosmetic composition for a long period of time.

A second invention is the cosmetic container of the first invention, wherein the hydrogen permeability of the hydrogen permeable sheet of one of the hydrogen storage portions is defined as lower than the hydrogen permeable sheet of another of the hydrogen storage portions.

A third invention is the cosmetic container of the second invention, wherein the hydrogen permeable sheet having a relatively high hydrogen permeability has a relatively small amount of hydrogen gas sealed therein, and the hydrogen permeable sheet having a relatively low hydrogen permeability has a relatively large amount of hydrogen gas sealed therein.

A fourth invention is the cosmetic container of any one of the first to third inventions, wherein one or a plurality of face masks are stored in the cosmetic container.

A fifth invention is the cosmetic container of the fourth invention, wherein the hydrogen storage portions are formed in a flat shape, and the main surface of the face mask and the main surface of the hydrogen storage portions are arranged so as to face each other.

Advantageous Effect of Invention

According to the cosmetic container of the present invention, it is possible to provide a cosmetic container capable of dissolving hydrogen into a cosmetic composition and maintaining a state in which hydrogen is dissolved for a long period of time.

BRIEF DESCRIPTION OF DRAWINGS

FIG. 3 is a conceptual diagram showing how hydrogen permeates the wall of the hydrogen storage portion.

DESCRIPTION OF EMBODIMENTS

First Embodiment

Preferred embodiments of the present invention will be described below with reference to the drawings. It should be noted that the description of configurations that can be appropriately implemented by those skilled in the art will be omitted and only the basic configuration of the present invention will be described. In the present specification, the cosmetic composition refers to a liquid cosmetic containing a colloid solution, specifically, including a beauty liquid, a cosmetic liquid, a dentifrice, or a bath preparation.

Figure 1:
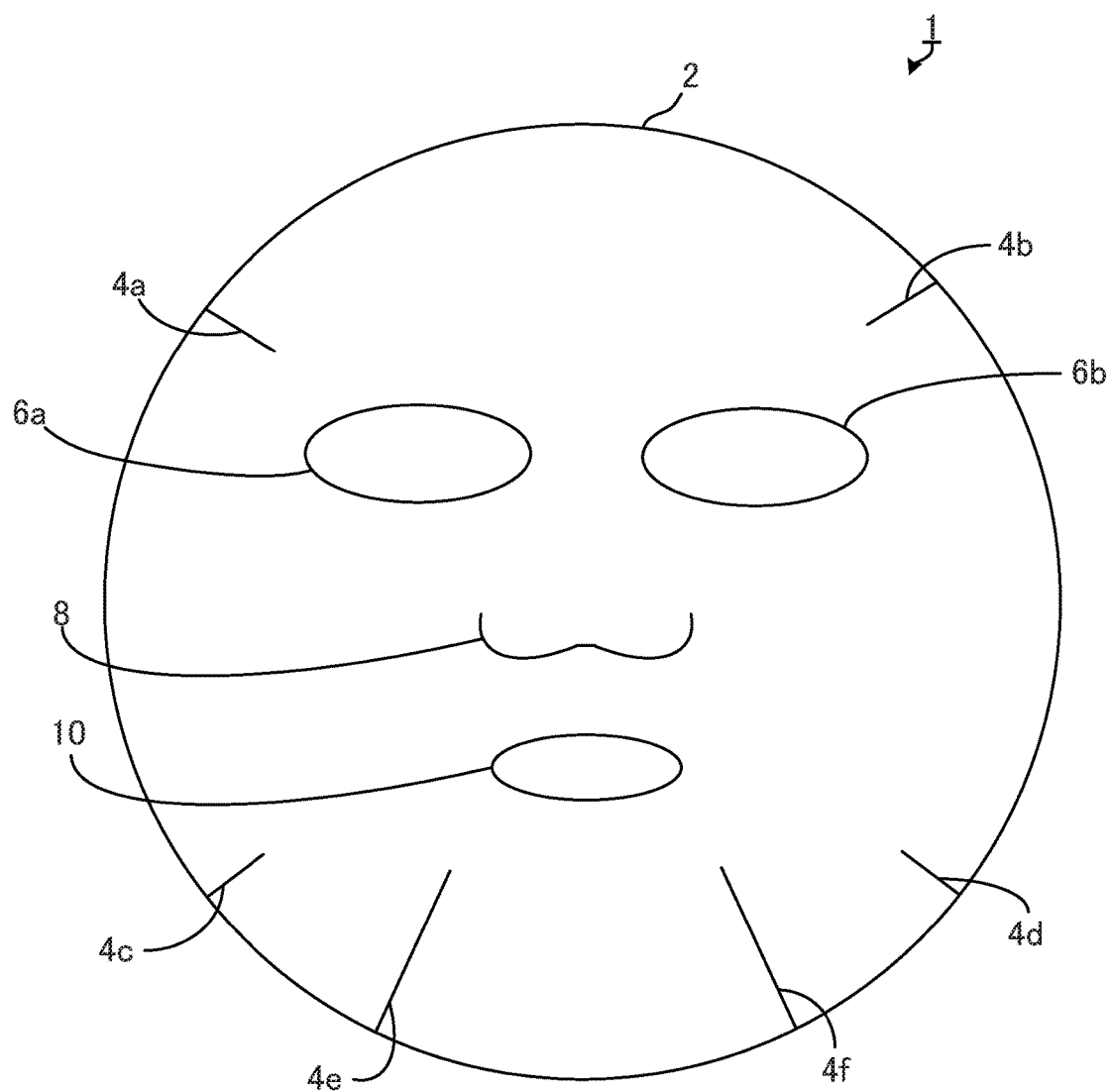
FIG. 1 is a schematic plan view of a face mask according to an embodiment of the present invention.

As illustrated in FIG. 1, the face mask 1 includes a base material sheet 2. The base material sheet 2 is formed of, for example, a nonwoven fabric. The nonwoven fabric material may be, for example, cupra, rayon, polyethylene, polyvinyl alcohol or the like. The base material sheet 2 is impregnated with a cosmetic composition.

The base material sheet 2 is configured so as to suitably cover the entire face of the user. For this purpose, cuts 4a, 4b, 4c, 4d, 4e and 4f are formed on the base material sheet 2 for conforming to the base material sheet 2 to the user's facial shape. In addition, the base material sheet 2 is formed with eye openings 6a and 6b for exposing the user's eyes and a mouth opening 10 for exposing the user's mouth. Further, a nose slit 8 is formed in the base material sheet 2 for conforming to the shape of the user's nose.

Figure 2:
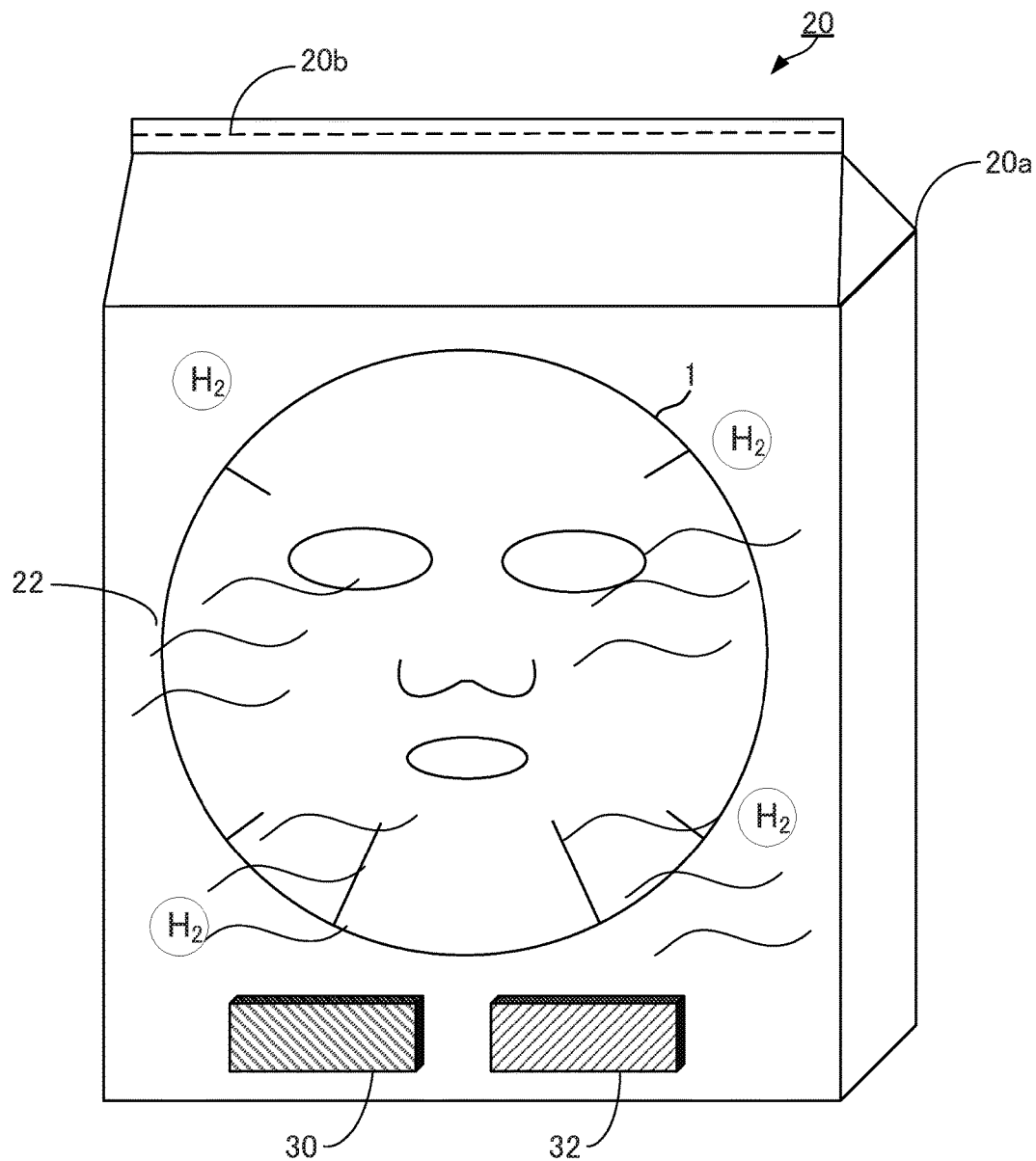
FIG. 2 is a schematic perspective view of a cosmetic container according to an embodiment of the present invention.

As illustrated in FIG. 2, the outermost layer of the cosmetic container 20 (hereinafter, referred to as "container 20") is a container main body 20a. The container main body 20a is formed of a hydrogen impermeable material. The hydrogen impermeable material may be, for example, a flexible multi-layered sheet used in boil-in-the-bag pouches, formed by carrying out a laminating processing using polyester (PET) as an outer layer, aluminum foil as an intermediate layer, and cast polypropylene (CPP) as an inner layer. A cutout portion 20b for taking out the face mask 1 is formed in the container main body 20a. By cutting away the cutout portion 20b, the face mask 1 within the container made able to be taken out.

A cosmetic composition 22 is stored in the container main body 20a. The main component of the cosmetic composition 22 is water and further contains, for example, at least one of the following beauty ingredients: human oligopeptide-1, human oligopeptide-13, acetylhexapeptide-8, palmitoylpentapeptide-4, water-soluble collagen, hydrolyzed collagen, succinoyl atelocollagen, magnesium ascorbyl phosphate, *Saccharomyces* (brown sugar, placenta extract) ferment liquid, sodium hyaluronate, sodium acetylated hyaluronate, sodium hyaluronate crosspolymer, cerebroside, arbutin, magnesium aspartate, dipotassium glycyrrhizate, copper gluconate, zinc gluconate, placenta extract, saitai extract, water soluble proteoglycan, platinum, sake cake extract, Iwabenkei root extract, apple fruit cultured cell extract, vitamin A oil, tocopherol, *Saccharomyces cerevisiae* extract, cerebroside, PCA-Na, natto gum, avocado oil, kaninabara fruit oil, apricot kernel oil, sunflower seed oil, sodium lysine dilauroyl glutamate, aminocaproic acid, or betaine.

Hydrogen storage portions 30 and 32 are provided inside the container main body 20a. At least a portion of the hydrogen storage portions 30 and 32 are formed of a hydrogen permeable sheet with hydrogen gas sealed therein. At least a portion of the surfaces of the hydrogen storage portions 30 and 32 are made of hydrogen permeable sheets. In this embodiment, one surface of the hydrogen storage portions 30 and 32 is a hydrogen permeable sheet 30a and 32a. A hydrogen permeable sheet means a sheet through which hydrogen permeates at a constant rate and corresponds to a regular plastic sheet. The extent to which hydrogen permeates (hydrogen permeability) can be adjusted by the material constituting the sheet. For example, mixing in silica decreases the permeating ratio of hydrogen.

The hydrogen storage portions 30 and 32 have different hydrogen permeabilities. The hydrogen permeability of the hydrogen permeable sheet 30a of the hydrogen storage portion 30 is larger than the hydrogen permeability of the hydrogen permeable sheet 32a of the hydrogen storage portion 32. The hydrogen permeable sheets 30a and 32a of the hydrogen storage portions 30 and 32 are formed so as to come into contact with the cosmetic composition 22 and the hydrogen permeating through the hydrogen permeable sheets 30a and 32a dissolves into the cosmetic composition 22.

As shown in FIG. 3, hydrogen is gradually discharged from the hydrogen storage portions 30 and 32 and dissolves into the cosmetic composition 22. As shown in FIG. 3(a), the hydrogen gas sealed in the hydrogen storage portion 30 permeates through the hydrogen permeable sheet 30a as indicated by an arrow X1. Similarly, as shown in FIG. 3(b), the hydrogen gas sealed in the hydrogen storage portion 32 permeates through the hydrogen permeable sheet 32a as indicated by the arrow X1. The hydrogen permeable sheet 32a has the same composition as that of the hydrogen permeable sheet 30a but is twice as thick and has low hydrogen permeability, for example, a hydrogen permeability of about 50% (percent) of the hydrogen permeable sheet 30a. Alternatively, as shown in FIG. 3(c), the hydrogen permeable sheet 32a and the hydrogen permeable sheet 30a may be formed with the same thickness, and making the hydrogen permeability of the hydrogen permeable sheet 32a lower than the hydrogen permeability of the hydrogen permeable sheet 30a by mixing more silica into the material of the hydrogen permeable sheet 32a than into the material of the hydrogen permeable sheet 30a.

Figure 4:
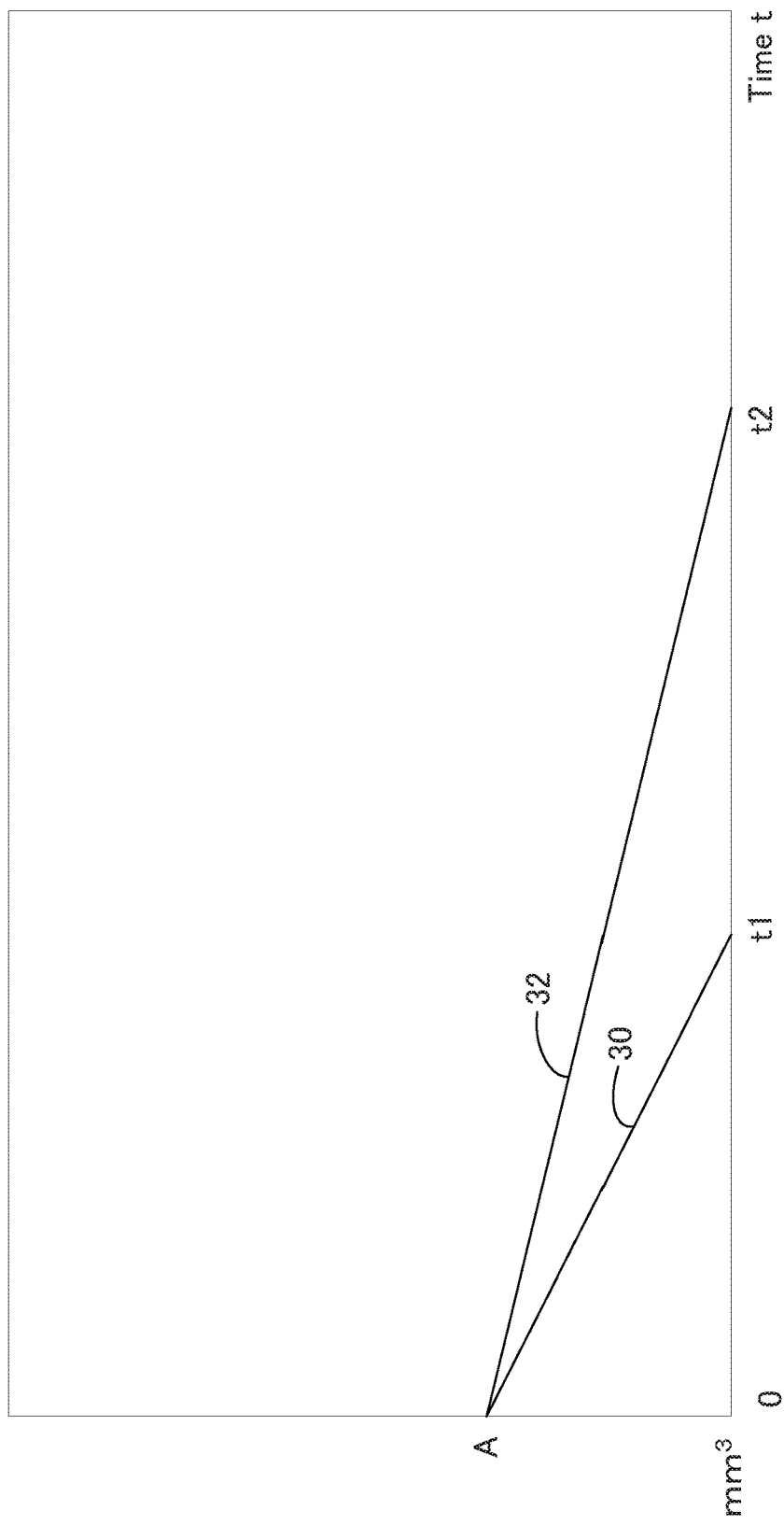
FIG. 4 is a conceptual diagram showing the amount of hydrogen in the hydrogen storage portion.

As shown in FIG. 4, although hydrogen gas of "A" mm$^3$ (cubic millimeters) is stored in the hydrogen storage portions 30 and 32, the hydrogen gas permeates through the hydrogen permeable sheets 30a and 32a and is gradually discharged. Hydrogen gas is exhausted from the hydrogen storage portion 30 at time t1, but discharge of hydrogen gas from the hydrogen storage portion 32 continues until time t2.

Figure 5:
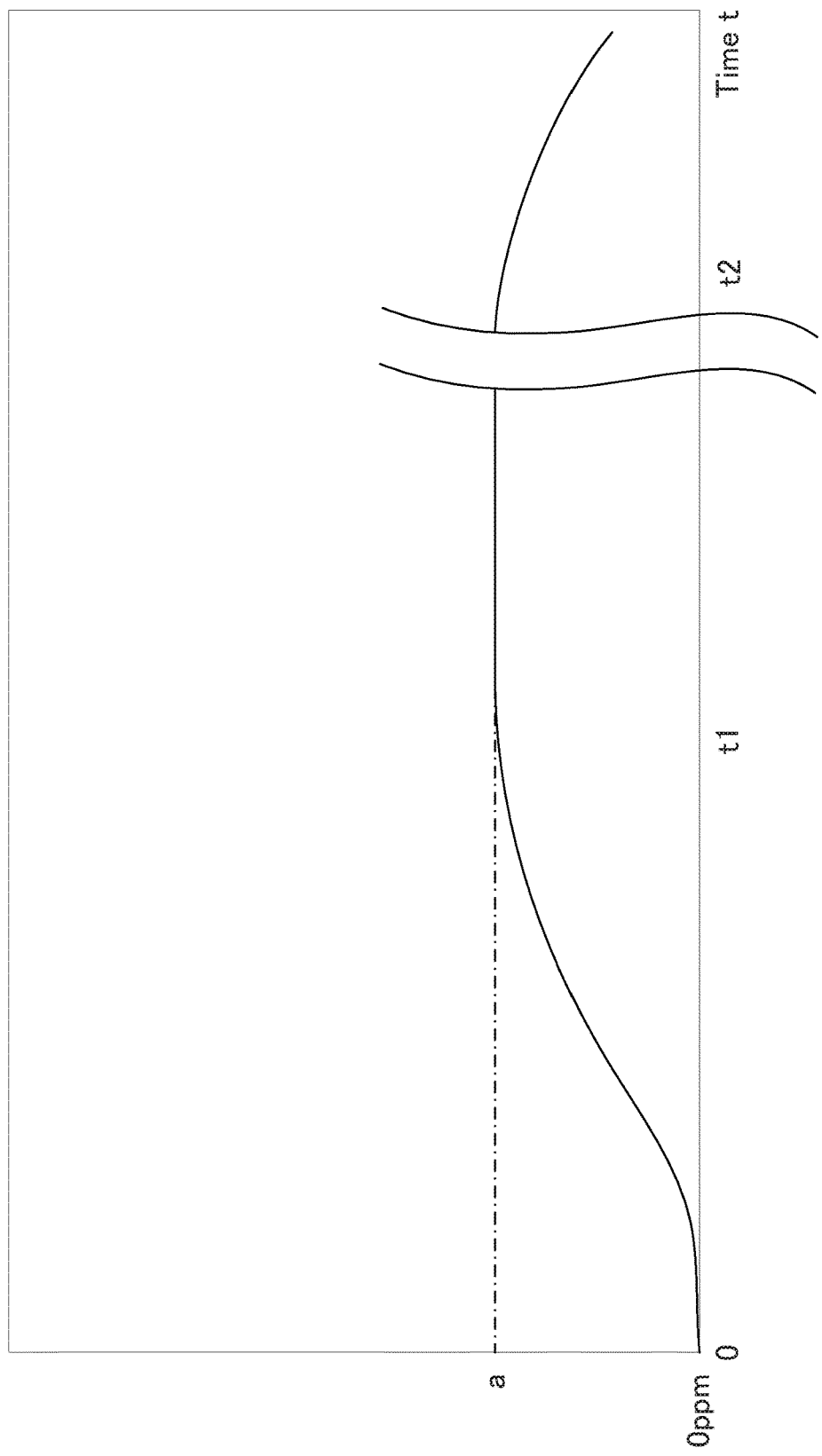
FIG. 5 is a conceptual diagram showing the hydrogen content in a cosmetic composition.

As shown in FIG. 5, the concentration of hydrogen gas contained in the cosmetic composition 22 increases until time t1, and becomes "a" ppm (parts per million). In the period leading up to the hydrogen content of the cosmetic composition 22 reaching "a" ppm, although a small amount of hydrogen gas escapes from the container main body 20a formed of a hydrogen impermeable material, and hydrogen gas also escapes from the cosmetic composition 22, since the amount of hydrogen gas discharged from the hydrogen storage portions 30 and 32 is larger than the amount of the hydrogen gas which escapes, the concentration of hydrogen gas contained in the cosmetic composition 22 increases until time t1. After time t1, the hydrogen gas is discharged only from the hydrogen storage portion 32. Since the amount of hydrogen gas escaping from the cosmetic composition 22 and the amount of hydrogen gas discharged from the hydrogen storage portion 32 and dissolved in the cosmetic composition 22 are substantially equal to each other, the concentration of hydrogen gas is maintained until time t2.

If the concentration of hydrogen gas dissolved in the cosmetic composition 22 is merely to be maintained for a long period of time, for example, it would be enough to provide the container 20 with only the hydrogen storage portion 32 and make the hydrogen permeability of the hydrogen permeable sheet 32a extremely low; however, in order to match the timing when the user uses the container 20 and the face mask 1, it is necessary to quickly raise the concentration of hydrogen gas dissolved in the cosmetic composition 22. After the amount of hydrogen gas dissolved in the cosmetic composition 22 reaches a predetermined concentration, it is necessary to maintain the concentration for a long period of time. For this purpose, the container 20 includes both the hydrogen storage portion 30 having a relatively high hydrogen permeability and the hydrogen storage portion 32 having a relatively low hydrogen permeability, and is formed so that the hydrogen storage portion 30 functions to increase the hydrogen content of the cosmetic composition 22 comparatively quickly and the hydrogen storage portion 32 functions mainly to maintain the hydrogen content of the cosmetic composition 22.

Second Embodiment

Figure 6:
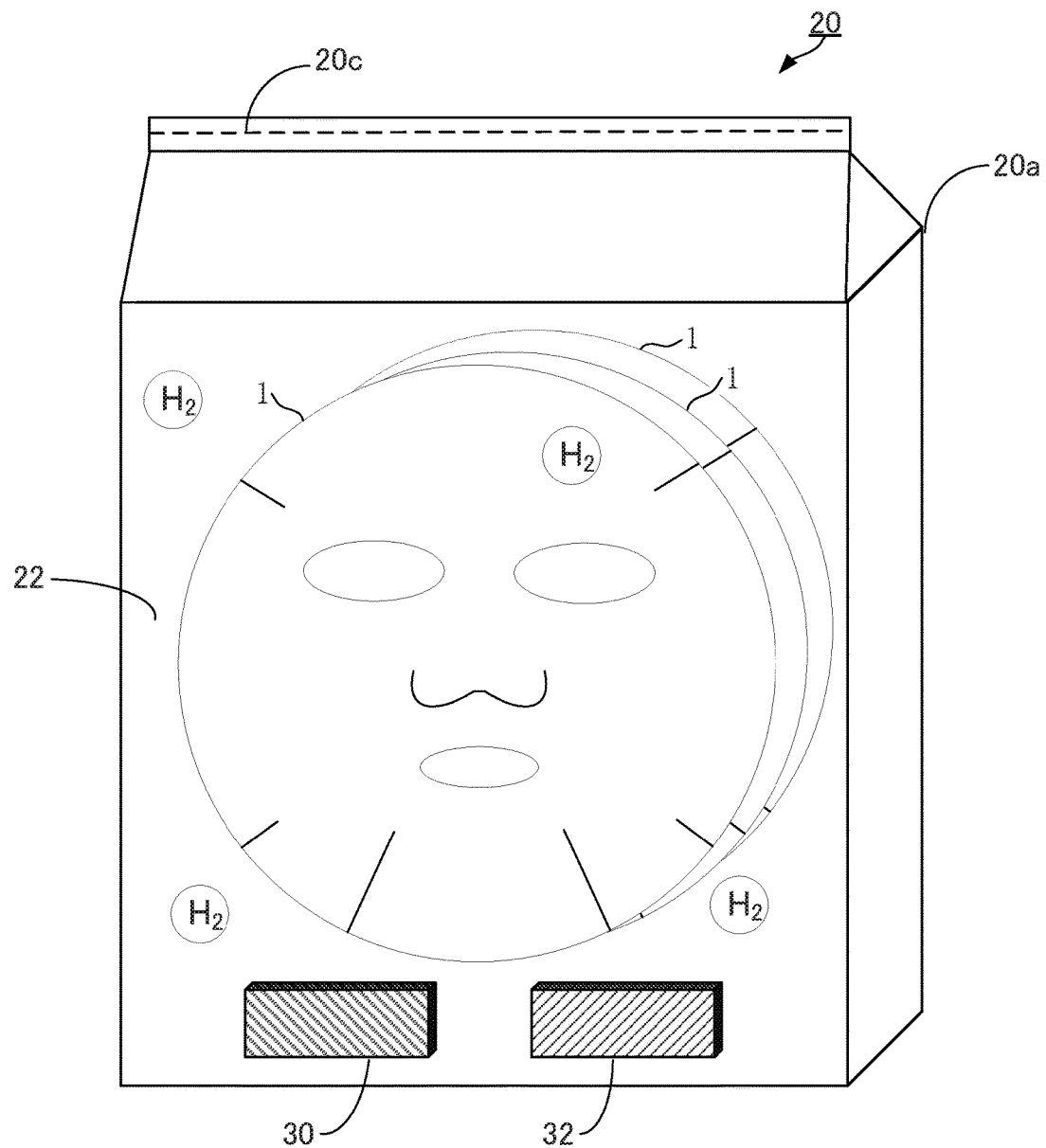
FIG. 6 is a schematic perspective view of a cosmetic container according to a second embodiment of the present invention.

A second embodiment will be described with reference to FIGS. 6 to 8. It should be noted that description of matters common to the first embodiment will be omitted. As illustrated in FIG. 6, the container 20 of the second embodiment stores a plurality of face masks 1. The container main body is formed with an openable/closable fastener 20c. The interior of the container 20 can be sealed by closing the fastener 20c. The fastener 20c may be, for example, a fastener called Ziploc (registered trademark).

Figure 7:
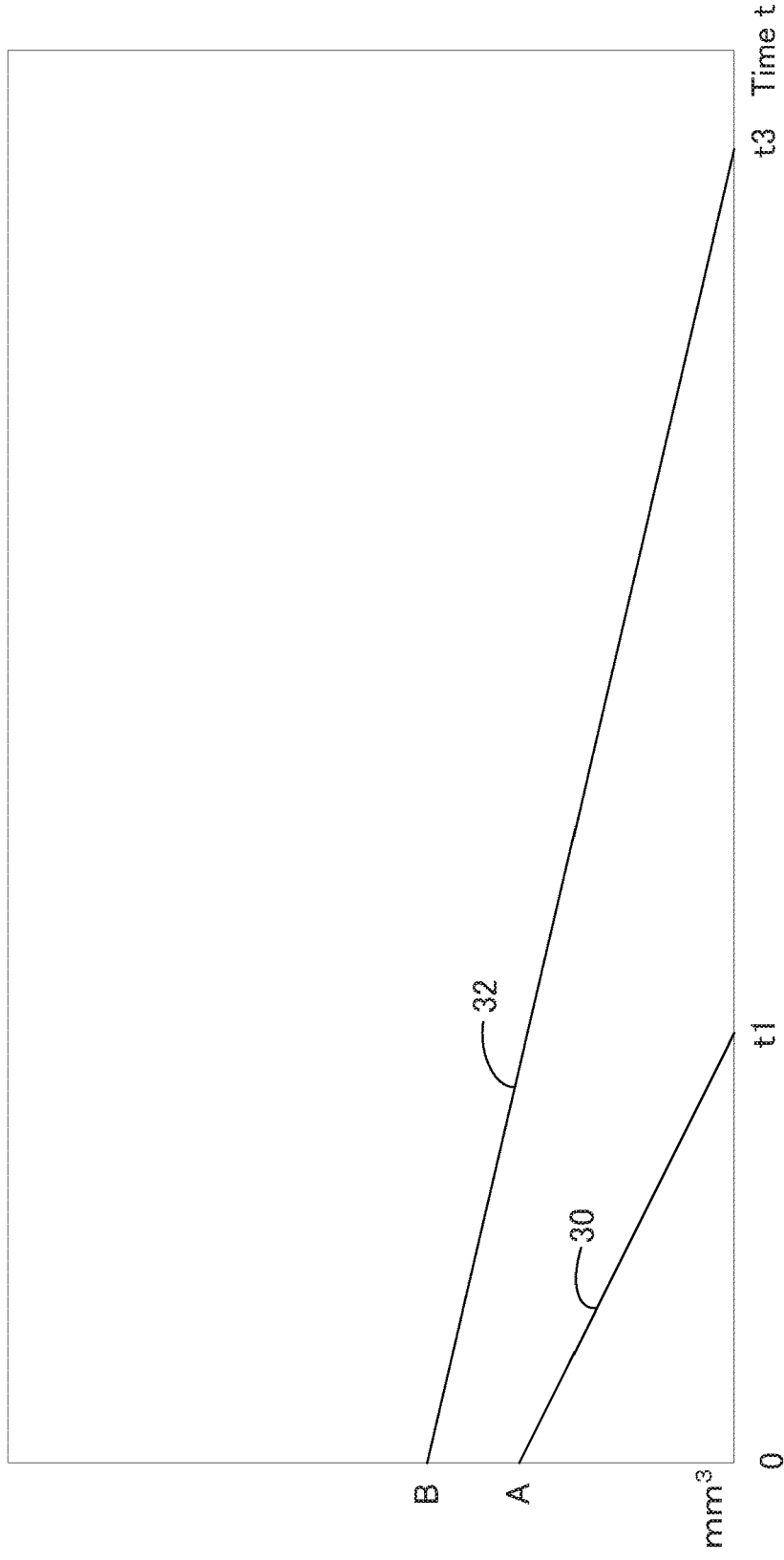
FIG. 7 is a conceptual diagram showing the amount of hydrogen in a hydrogen storage portion.

As shown in FIG. 7, the hydrogen storage portion 30 is filled with "A" $mm^3$ of hydrogen gas, and the hydrogen storage portion 32 contains a greater amount, "B" $mm^3$, of hydrogen gas. For this purpose, even when the hydrogen gas sealed in the hydrogen storage portion 30 is exhausted, the hydrogen gas continues to be discharged from the hydrogen storage portion 32 for a long period of time.

Figure 8:
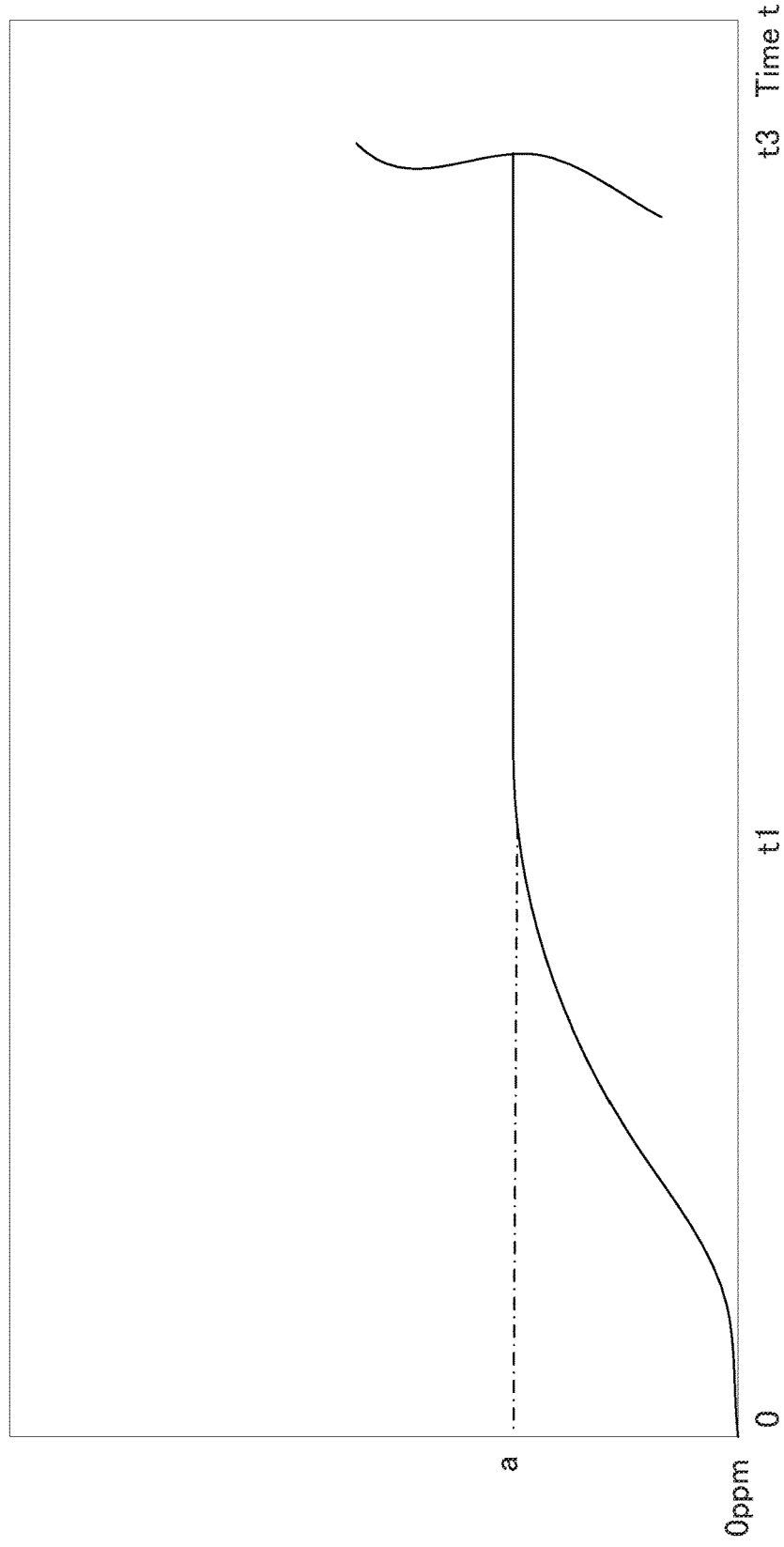
FIG. 8 is a conceptual diagram showing the hydrogen content in a cosmetic composition.

As shown in FIG. 8, the concentration of hydrogen gas contained in the cosmetic composition 22 increases until time t1. Even in the period leading up to time t1, although a small amount of hydrogen gas escapes from the container main body 20a and hydrogen gas also escapes from the cosmetic composition 22, since the amount of hydrogen gas discharged from the hydrogen storage portions 30 and 32 is larger than the amount of hydrogen gas escaping, the concentration of hydrogen gas contained in the cosmetic composition 22 increases until time t1. After time t1, the hydrogen gas is discharged only from the hydrogen storage portion 32. The amount of hydrogen gas escaping from the cosmetic composition 22 and the amount of hydrogen gas discharged from the hydrogen storage portion 32 and dissolved in the cosmetic composition 22 are almost equal to each other; however, since the amount of hydrogen gas sealed in the hydrogen storage portion 32 is larger than the amount of hydrogen gas sealed in the hydrogen storage portion 30, the hydrogen content is maintained until time t3.

Third Embodiment

Figure 9:
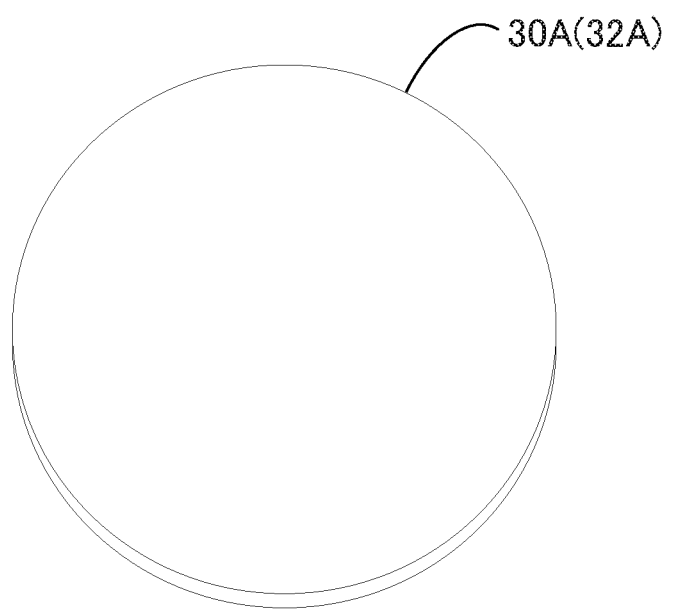
FIG. 9 is a schematic perspective view of a hydrogen storage portion according to a third embodiment of the present invention.
Figure 10:
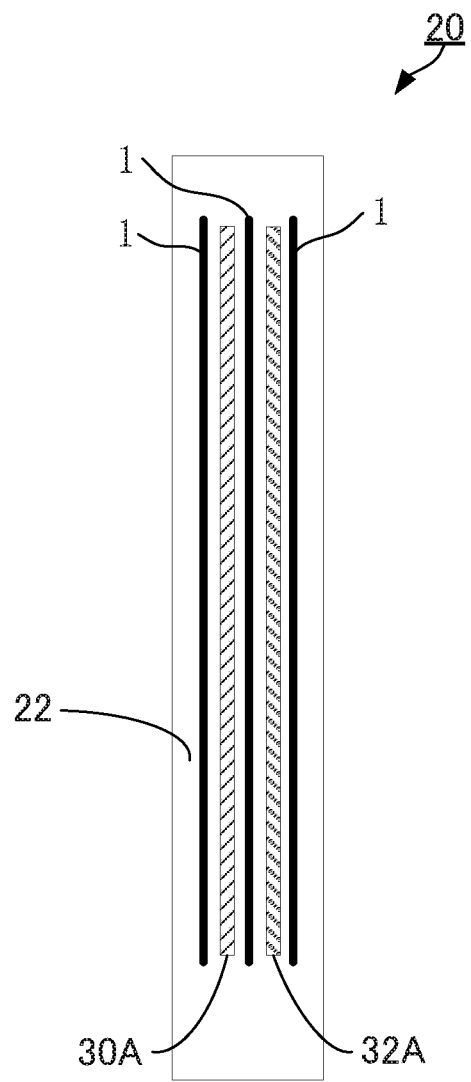
FIG. 10 is a schematic side view of a cosmetic container according to a third embodiment of the present invention.

A third embodiment will be described with reference to FIGS. 9 and 10. It should be noted that description of matters common to the second embodiment will be omitted. As illustrated in FIG. 9, the hydrogen storage portions 30A and 32A are formed flat; and as illustrated in FIG. 10, the main surface of the face mask 1 and the main surfaces of the hydrogen storage portions 30A and 32A are arranged so as to face each other. In FIG. 10, the hydrogen storage portions 30A and 32A are arranged between the plurality of face masks 1.

As a result, the hydrogen gas easily dissolves into the cosmetic composition 22 impregnated in the face mask 1.

It should be noted that the cosmetic container of the present invention is not limited to the above embodiments, and various modifications can be made without departing from the gist of the present invention.

REFERENCES SIGNS LIST

1 Face mask
2 Base material sheet
20 Cosmetic container
22 Cosmetic composition
30, 30A, 32A Hydrogen storage portions
30a, 32a Hydrogen permeable sheets

The invention claimed is:

1. A cosmetic container for storing a cosmetic composition, comprising:
    a container main body formed of a hydrogen impermeable material;
    a plurality of hydrogen storage portions filled with hydrogen gas, at least one of which is formed of a hydrogen permeable sheet, wherein the hydrogen permeability of the hydrogen permeable sheet through which hydrogen gas permeates is configured to be different among the plurality of the hydrogen storage portions; and
    the hydrogen permeable sheets of the plurality of the hydrogen storage portions are configured so as to come into close contact with the cosmetic composition stored in the container main body.

2. The cosmetic container according to claim 1, wherein the hydrogen permeability of the hydrogen permeable sheet of one of the hydrogen storage portions is defined as lower than the hydrogen permeable sheet of another of the hydrogen storage portions.

3. The cosmetic container according to claim 2, wherein the hydrogen permeable sheet having a relatively high hydrogen permeability has a relatively small amount of hydrogen gas sealed therein, and the hydrogen permeable sheet having a relatively low hydrogen permeability has a relatively large amount of hydrogen gas sealed therein.

4. The cosmetic container according to claim 3, wherein one or more of the face mask is stored in the cosmetic container.

5. The cosmetic container according to claim 4, wherein the hydrogen storage portions are formed in a flat shape, and the main surface of the face mask and the main surface of the hydrogen storage portions are arranged so as to face each other.

6. The cosmetic container according to claim 2, wherein one or more of the face mask is stored in the cosmetic container.

7. The cosmetic container according to claim 6, wherein the hydrogen storage portions are formed in a flat shape, and the main surface of the face mask and the main surface of the hydrogen storage portions are arranged so as to face each other.

8. The cosmetic container according to claim 1, wherein one or more of a face mask is stored in the cosmetic container.

9. The cosmetic container according to claim 8, wherein the hydrogen storage portions are formed in a flat shape, and the main surface of the face mask and the main surface of the hydrogen storage portions are arranged so as to face each other.

\* \* \* \* \*